(12) United States Patent
Spoettl et al.

(10) Patent No.: US 10,585,034 B2
(45) Date of Patent: Mar. 10, 2020

(54) SMART CARD MODULE, METHOD FOR PRODUCING A SMART CARD MODULE, SMART CARD AND METHOD FOR TESTING A SMART CARD MODULE

(71) Applicant: Infineon Technologies AG, Neubiberg (DE)

(72) Inventors: Thomas Spoettl, Mintraching (DE); Mathias Belzner, Cadolzburg (DE); Ralph Domnick, Buckendorf (DE); Jens Pohl, Bernhardswald (DE); Frank Pueschner, Kelheim (DE); Peter Stampka, Burglengenfeld (DE); Daniel Weiss, Hessdorf (DE)

(73) Assignee: Infineon Technologies AG, Neubiberg (DE)

( * ) Notice: Subject to any disclaimer, the term of this patent is extended or adjusted under 35 U.S.C. 154(b) by 34 days.

(21) Appl. No.: 16/043,824

(22) Filed: Jul. 24, 2018

(65) Prior Publication Data
US 2019/0033206 A1  Jan. 31, 2019

(30) Foreign Application Priority Data
Jul. 25, 2017 (DE) .......................... 10 2017 116 736

(51) Int. Cl.
*G01N 21/25* (2006.01)
*G02B 5/08* (2006.01)
(Continued)

(52) U.S. Cl.
CPC ......... *G01N 21/255* (2013.01); *B42D 25/305* (2014.10); *B42D 25/324* (2014.10); *B42D 25/351* (2014.10); *B42D 25/36* (2014.10); *B42D 25/373* (2014.10); *G01N 21/251* (2013.01); *G02B 5/0875* (2013.01); *G06K 19/06009* (2013.01); *G06K 19/06028* (2013.01);
(Continued)

(58) Field of Classification Search
None
See application file for complete search history.

(56) References Cited

U.S. PATENT DOCUMENTS

| | | | |
|---|---|---|---|
| 2004/0101676 A1* | 5/2004 | Phillips | B32B 27/36 428/323 |
| 2014/0211332 A1* | 7/2014 | Krasnov | C03C 17/36 359/838 |

(Continued)

FOREIGN PATENT DOCUMENTS

| | | |
|---|---|---|
| DE | 4445822 A1 | 6/1996 |
| DE | 69629743 T2 | 7/2004 |

(Continued)

*Primary Examiner* — Shawn Decenzo
(74) *Attorney, Agent, or Firm* — Murphy, Bilak & Homiller, PLLC

(57) ABSTRACT

In various exemplary embodiments, a smart card module is provided. The smart card module includes a carrier and a layer stack at least partly covering the carrier. The layer stack includes a reflection layer, a light-transmissive layer arranged above the reflection layer, and a partly light-transmissive silver layer arranged above the light-transmissive layer. The partly light-transmissive silver layer is configured for reflecting part of light impinging on the partly light-transmissive silver layer.

21 Claims, 9 Drawing Sheets

(51) Int. Cl.

| | |
|---|---|
| *G06K 19/06* | (2006.01) |
| *G06K 19/07* | (2006.01) |
| *B42D 25/324* | (2014.01) |
| *B42D 25/305* | (2014.01) |
| *B42D 25/36* | (2014.01) |
| *B42D 25/351* | (2014.01) |
| *B42D 25/373* | (2014.01) |

(52) U.S. Cl.
CPC ....... *G06K 19/06037* (2013.01); *G06K 19/07* (2013.01); *G06K 19/0723* (2013.01)

(56) References Cited

U.S. PATENT DOCUMENTS

| | | | |
|---|---|---|---|
| 2014/0218663 A1* | 8/2014 | Stahl | B42D 25/29 |
| | | | 349/86 |
| 2014/0339298 A1* | 11/2014 | Lacoste | C09J 7/29 |
| | | | 235/375 |
| 2016/0183351 A1* | 6/2016 | Snyder | H04L 12/10 |
| | | | 315/152 |
| 2018/0001691 A1* | 1/2018 | Harada | D21H 21/42 |
| 2018/0121643 A1* | 5/2018 | Talwerdi | G06F 21/32 |
| 2019/0001732 A1* | 1/2019 | Ongsitco | G06Q 20/3278 |
| 2019/0039403 A1* | 2/2019 | Whiteman | B42D 25/40 |
| 2019/0066094 A1* | 2/2019 | Bae | G06Q 20/16 |

FOREIGN PATENT DOCUMENTS

| | | |
|---|---|---|
| DE | 102011119598 A1 | 5/2013 |
| DE | 102013113340 A1 | 6/2015 |

\* cited by examiner

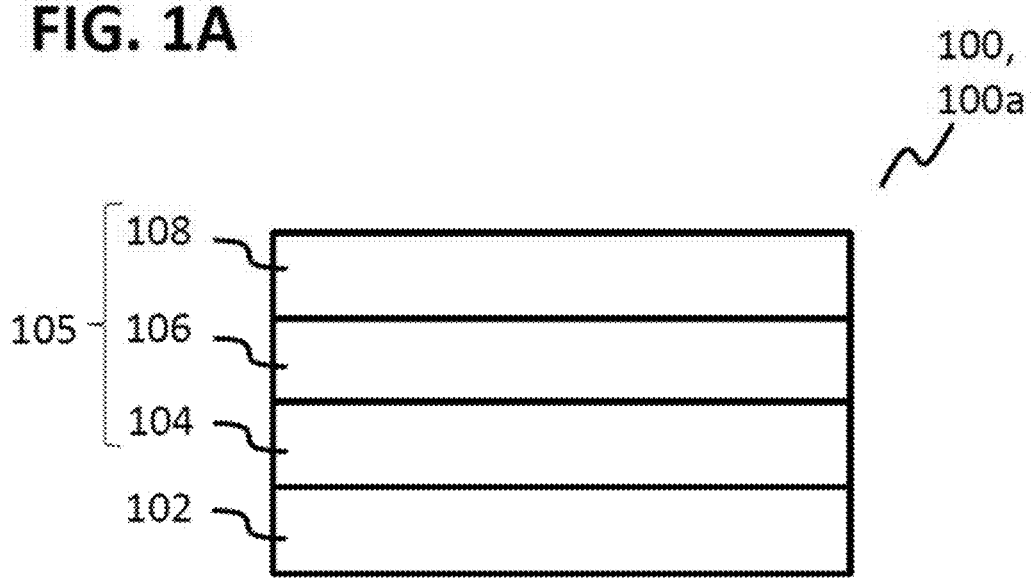
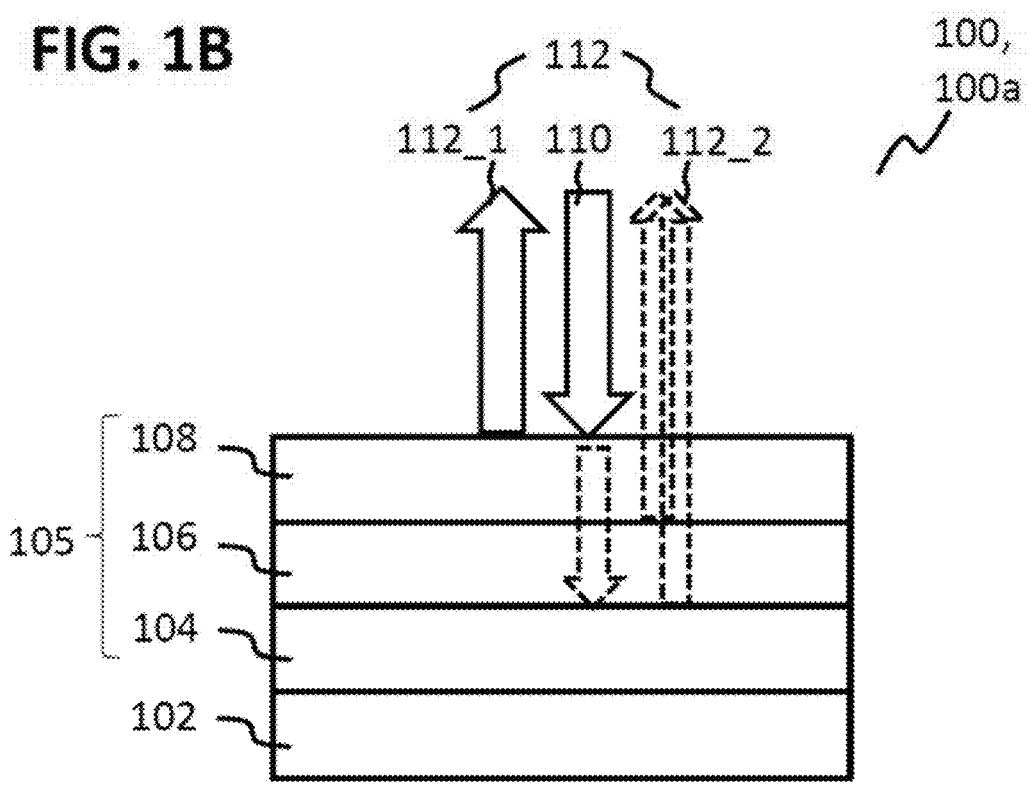

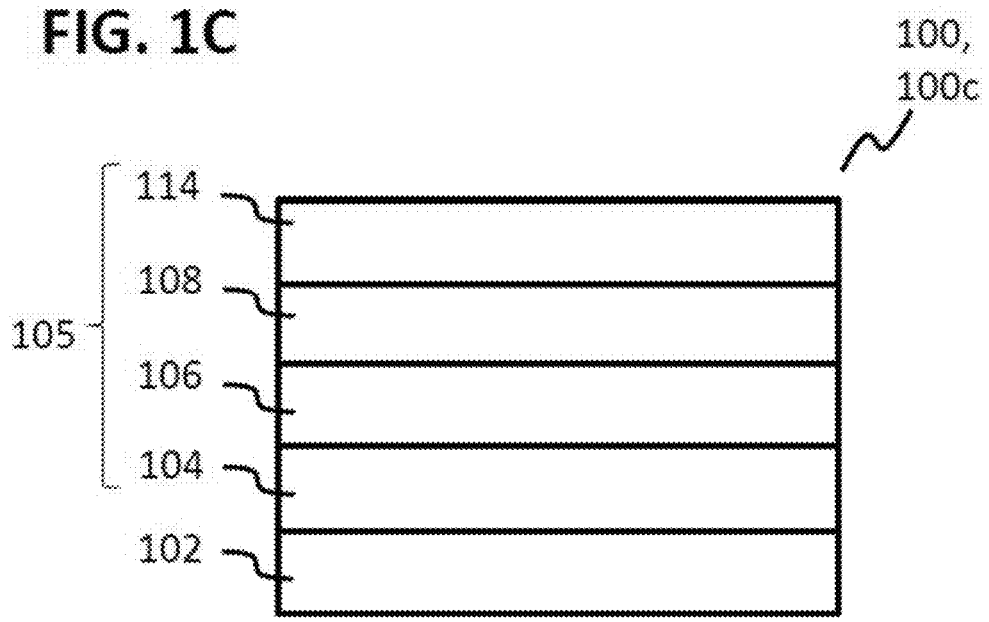
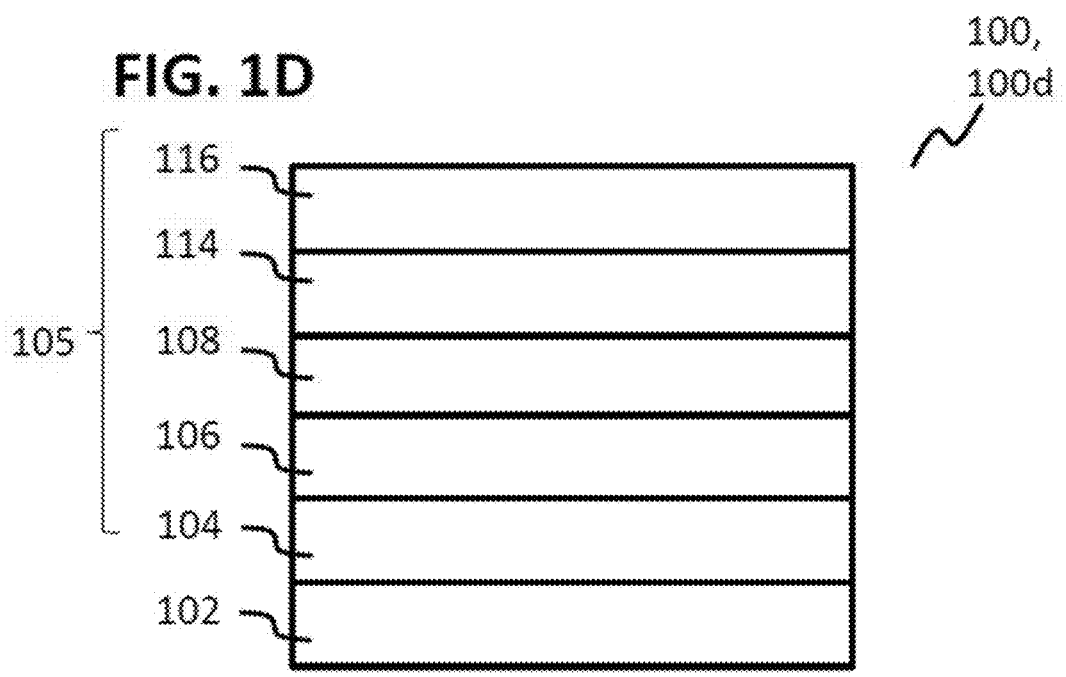

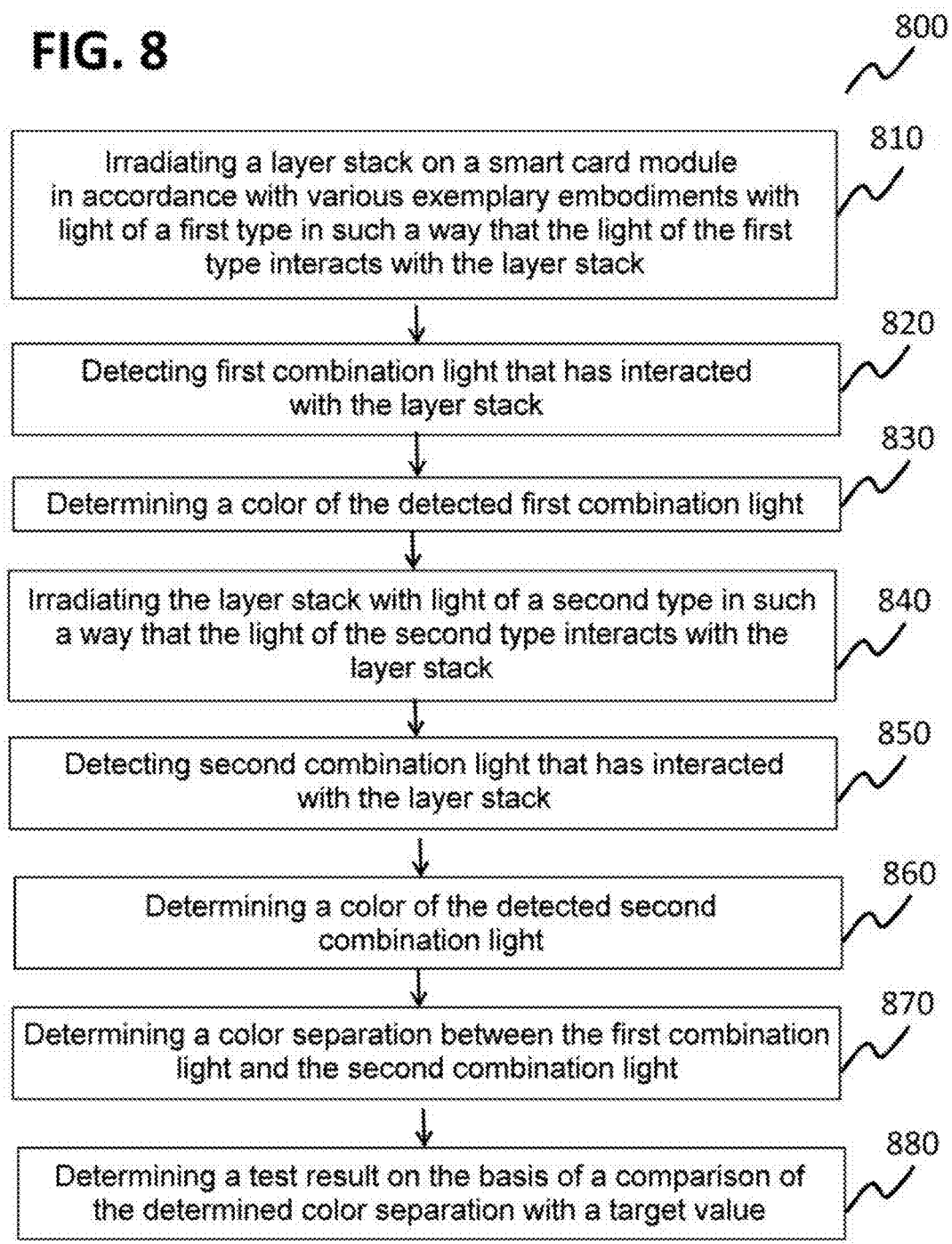

SMART CARD MODULE, METHOD FOR PRODUCING A SMART CARD MODULE, SMART CARD AND METHOD FOR TESTING A SMART CARD MODULE

PRIORITY CLAIM

This application claims priority to German Patent Application No. 10 2017 116 736.6, filed on 25 Jul. 2017, the content of said German application incorporated herein by reference in its entirety.

TECHNICAL FIELD

Various embodiments generally relate to a smart card module, a method for producing a smart card module, a smart card and a method for testing a smart card module.

BACKGROUND

Conventional smart card modules can be provided with markings by means of special inks, holograms or barcodes, which markings can be read out either just visually or by means of special devices (for example UV measuring devices). Owing to their manner of production, said markings can be copied by means of appropriate know-how and effort. Visual read-out can be susceptible to errors. Using special equipment for the read-out can be complicated (place test item beneath test device, etc.) and/or—depending on the device required—expensive.

SUMMARY

In various exemplary embodiments, a thin-film system is provided which can be used to ascertain authenticity in various applications such as, for example, smart card modules (contact-based, contactless, dual interface, without (electronic) chip), electronic identification documents (eID documents) comprising smart card modules (contact-based, contactless, dual interface, without (electronic) chip). A smart card module without an electronic chip can be understood to mean for example a semiconductor lamina (e.g. a silicon lamina) which can be provided with a security feature and may have been or can be laminated into a smart card, for example, but does not have its own circuit.

In various exemplary embodiments, upon varying illumination, the thin-film system can have different selective light reflection, which can be readable both visually and using a cellular phone and/or a photometer. Owing to its material combination, the layer can be virtually uncopiable. Moreover, the effect can be discernible easily and rapidly.

In various exemplary embodiments, the thin-film system (also referred to as layer stack or layer system) may have been or can be applied on a metal surface (for example gold (Au), palladium (Pd), nickel (Ni), iron (Fe), copper (Cu), aluminum (Al) or steel) or on silicon (Si).

In various exemplary embodiments, a layer combination may have been or can be applied on the metal or silicon surface by means of a physical vapor deposition (PVD). Upon varying illumination at a measurement point the layer system (the layer stack) can have a diffuse scattering effect and a selective light reflection, which cannot be copiable in this combination by means of other methods such as ink printing, for example. This special behavior (interaction with incident light) can provide a high forgery-proofness. Moreover, the layer stack can be mountable on different surfaces.

In various exemplary embodiments, the layer system can comprise a metallic mirror, one or more light-transmissive (e.g. translucent or transparent) spacer layers and a semitransparent silver layer.

In various exemplary embodiments, the layer system can furthermore comprise one or more transparent cover layers.

Substantially any arbitrary color can be produced by suitable selection of the materials and layer thicknesses, wherein, by means of the light-transmissive layer arranged above the metallic mirror, an interference-like effect (also referred to as Fabry-Perot effect) can be generated, i.e. amplification of the incident light of that (those) wavelength(s) for which a constructive interference is generated by the light-transmissive layer arranged above the mirror layer.

Upon irradiation of the layer stack with light, light that has interacted with the layer stack and is reflected back (emitted) by the layer stack can have two components: a light component reflected directly by the semitransparent (partly transmissive) silver layer (also referred to as reflection component or reflection light), and a component which can be based on light which is transmitted by the partly transmissive silver layer to the mirror layer and which can form a constructive interference of light specularly reflected at a surface of the transparent layer and the mirror layer (also referred to as interference portion or interference light). The light that has interacted with the layer stack and is reflected back (emitted) by the layer stack can therefore also be referred to as combination light.

In other words, a second, surface-morphology-based color reflection can also be superimposed on the (interference) light based on the Fabry-Perot effect, which color reflection can differ significantly from the interference light. That is to say that a directionally reflected radiation and a (different-colored) radiation can be present in the combination light. Therefore, given a fixed viewing angle, two colors can be clearly distinguishable metrologically (e.g. by means of a spectrometer). Upon examination with the naked eye, it may be necessary to change the viewing angle in order to be able to perceive the different colors, e.g. as an angle-dependent color change.

In various exemplary embodiments, properties of the combination light (color, intensity) can have angle dependencies on an angle of incidence at which the layer stack is illuminated by means of a light source, and also on a viewing angle at which the layer stack is viewed or picked up during illumination, and also on an angle between the angle of incidence and the viewing angle. While the reflection component can have the angle dependence substantially with regard to its intensity, the interference component can have the angle dependence with regard to its color (and possibly with regard to its intensity), since, with a change in the angle of incidence and/or the viewing angle, a layer thickness of the light-transmissive layer through which radiation is transmitted changes, and thus so does a wavelength of light for which constructive interference is possible. The angle dependencies of the combination light can be known (e.g. be calculated) given a known layer construction and can be taken into account in a test of a layer stack, e.g. when checking the authenticity of a smart card module.

Not only smooth surfaces but also suitable rough surfaces can likewise have the effect described. In various exemplary embodiments, the semitransparent silver layer may have been or can be modified, e.g. roughened, by means of laser treatment such that the surface forms many small mirrors. As a result, the incident light can be reflected anisotropically (in a mirror-like manner). As a result, at the same time, sufficiently (small) planar coated surfaces can also arise, by which the radiation (on account of the "nanomorphology" thereof) is diffusely scattered and can appear in a significantly, measurably different color (than the interference color) that can be utilized for the purposes of checking authenticity.

In various exemplary embodiments, the effect described can be designable such that no color difference is discernible to the human eye (upon illumination with different types of light). This is possible using multilayer systems which generate a constructive interference of light rays impinging on their surface in such a way that the combination spectrum remains substantially or totally unchanged in the range of visible light, i.e. of approximately 380-780 nm, but differs significantly from one another in the near-infrared or infrared range (NIR or IR) or in the ultraviolet (UV) range.

In various exemplary embodiments, a method for determining the two-color characteristic (e.g. using daylight and flash light) can be provided. In various exemplary embodiments, the method can be used for checking authenticity (e.g. of the smart card module).

In various exemplary embodiments, a portable data processing device, e.g. a smartphone, a tablet or the like, can be used for the method. The method can be carried out for example by means of an application program (a so-called app). It is thus possible to provide a cost-effective system for checking authenticity which is easy to use and which can be made accessible to a large group of people, if appropriate, since smartphones are in widespread use.

In various exemplary embodiments, forgery-proof PVD layers can be provided which can be applied on substantially arbitrary surfaces and which have one specific color (e.g. blue) upon illumination with light of a first type (e.g. in the case of daylight) and exhibit a different color (e.g. yellow) upon illumination with light of a second type, e.g. under direct illumination, e.g. by means of a flashlamp or of a flash light, e.g. of a smartphone. In various exemplary embodiments, this two-color characteristic can be identified and used for checking authenticity, e.g. by means of a smartphone app.

In various exemplary embodiments, the color change effect can be tested in detail with the aid of a spectrometer.

In various exemplary embodiments, a first measurement can be carried out with perpendicularly incident light. In a wavelength range of 400-1000 nm, the intensity of the reflected light beam can be detected. In a further measurement, a lateral light source can be engaged as well. The light intensity of the reflection of the perpendicularly incident light can increase in the case of the forgery-proof layer. To summarize, in various exemplary embodiments, the forgery-proofness of the layer can be based on the fact that there is a maximum light reflection at at least one wavelength and the layer stack simultaneously exhibits scattering properties of a mechanically rough surface.

In various exemplary embodiments, a reliability can be significantly increased by firstly generating a geometric pattern, which can be used for example as a position reference, by selectively removing the layer stack using the laser beam. Alternatively, the surface structure of the module surface of the smart card module itself can also be used for this purpose.

In various exemplary embodiments, using the laser it is then possible to treat a region, e.g. a small area, a symbol, a letter or the like, of the coated surface (e.g. of the light-transmissive layer) such that the color thereof changes significantly, for example by means of changing a layer thickness of the light-transmissive layer by means of the laser.

Under "normal" conditions, for example in the case of daylight, the layer can appear in a first color, e.g. blue, and under direct illumination (e.g. by means of a flashlamp, flash light of the smartphone or the like) in a second color, e.g. yellow. The laser-treated location can appear for example firstly (e.g. in the case of daylight) in a third color, e.g. green, and then, e.g. under the direct illumination, in a fourth color, e.g. red.

In various exemplary embodiments, an evaluation can be carried out in such a way that firstly color values (e.g. L*a*b* values) of the four different colors together with certain tolerance ranges are determined and stored in an app.

In various exemplary embodiments, checking authenticity can be carried out, e.g. by means of the app, in such a way that after the app has been activated, the geometric pattern (as position reference) is sighted by the smartphone camera in such a way that the geometric pattern appears at a center or some other target position displayed on a display of the smartphone. After recognition of the geometric pattern, in various exemplary embodiments, with the aid of a photograph—taken e.g. during illumination of the layer stack with daylight—of this location at two previously defined positions in the vicinity of the geometric pattern (1× on the coated module surface and 1× on the one laser-treated location), the color values associated with the first type of light can be determined, correlated with one another and compared with values stored in the app.

By means of a second photograph, which represents the same location, this time during illumination with a different type of light, e.g. flash light, the color values assigned to the different type of light are then recorded at the same positions and are correlated with one another.

If the values respectively correlated with one another then correspond to the internal reference and have a predetermined color separation from one another, it can be ascertained with high reliability that the identification or the product is an original.

In various exemplary embodiments, instead of the two color change components, just one color change components or more than two color change components can be used for checking authenticity.

In various exemplary embodiments, a QR code or a barcode may have been or can be applied on the smart card module in such a way that it has been or is mounted on the layer stack and/or on the geometric pattern. This can make it possible to generate a forgery-proof QR code/barcode that can be used for individualization/personalization.

In various exemplary embodiments, encrypted information of the QR code/barcode can additionally be stored in the chip (e.g. in the integrated circuit (IC)) and be read out as necessary, e.g. by means of NFC using the smartphone or some other suitable reader. In accordance with various exemplary embodiments, the security layer having optionally extendable security yields multilevel security in the ultimate layout.

By means of the smartphone, in various exemplary embodiments, it is possible to detect even a spectrum that is invisible to the human eye, e.g. a reflection in the near IR (near-infrared range starting from 780 nm), since conventional smartphone camera detector chips are sensitive in the near-infrared range. In the case of photographic cameras, this is disturbing and is compensated for by filters, this does not happen in the case of smartphones. Smartphone cameras and other detector devices which are sensitive in a wavelength range that is invisible to the human eye, e.g. cameras, photometers and/or spectrometers which (also) detect in the near-infrared range and/or the UV range, can be used in various exemplary embodiments in order that a layer stack formed such that the color change takes place in a wavelength range (e.g. UV, NIR) that is invisible to the human eye is subjected to checking of authenticity.

In various exemplary embodiments, a smart card module is provided. The smart card module can comprise a carrier and a layer stack at least partly covering the carrier. The layer stack can comprise a reflection layer, a light-transmissive layer arranged above the reflection layer, and a partly light-transmissive silver layer arranged above the light-transmissive layer and configured for reflecting part of light impinging on said silver layer.

In various exemplary embodiments, a thickness of the light-transmissive layer can be designed such that a constructive interference for generating interference light is made possible for at least one wavelength of light impinging on the silver layer.

In various exemplary embodiments, the thickness of the light-transmissive layer can be in a range of approximately 40 nm to approximately 400 nm.

In various exemplary embodiments, the layer thickness of the light-transmissive layer for enabling a constructive interference in a wavelength range of blue light can be in a range of approximately 70 nm to approximately 110 nm, optionally in a range of approximately 80 nm to approximately 100 nm, and/or for enabling a constructive interference in a wavelength range of yellow light is in a range of approximately 120 nm to approximately 180 nm, optionally in a range of approximately 135 nm to approximately 165 nm.

In various exemplary embodiments, a thickness of the partly light-transmissive silver layer can be in a range of approximately 2 nm to approximately 25 nm.

In various exemplary embodiments, the silver layer can have a rough surface structure, such that the reflected part of light impinging on it is diffusely reflected.

In various exemplary embodiments, the layer stack can be configured for forming combination light from the reflected light and the interference light upon irradiation with light, and be configured in such a way that the combination light has a first combination color upon irradiation with a first type of light, and that the combination light has a second combination color upon irradiation with a second type of light, wherein a spectrum of the first type of light and a spectrum of the second type of light differ from one another at least in a wavelength range of the interference light, such that the first combination color differs from the second combination color.

In various exemplary embodiments, the smart card module can furthermore comprise a further layer stack, which can be configured in such a way that the combination light has a third combination color upon irradiation with the first type of light, and that the combination light has a fourth combination color upon irradiation with the second type of light, wherein a spectrum of the first type of light and a spectrum of the second type of light differ from one another at least in a wavelength range of the interference light of the further layer stack, such that the third combination color differs from the fourth combination color.

In various exemplary embodiments, the first combination color and the third combination color can have a color separation with respect to one another which is less than a color difference perception threshold for a human being, for example a color separation $\Delta E<1$.

In various exemplary embodiments, the first combination color and the third combination color can have a color separation with respect to one another which is greater than or equal to a color difference perception threshold for a human being, for example a color separation $\Delta E \geq 1$.

In various exemplary embodiments, the smart card module can furthermore comprise at least one electrically insulating or electrically conductive cover layer arranged above the silver layer.

In various exemplary embodiments, a smart card is provided. The smart card can comprise a smart card body and a smart card module in accordance with various exemplary embodiments embedded into the smart card body.

In various exemplary embodiments, a method for producing a smart card module is provided. The method can comprise forming a reflection layer above a carrier in such a way that the reflection layer at least partly covers the carrier, arranging a light-transmissive layer above the reflection layer, and arranging a partly light-transmissive silver layer, which can be configured for reflecting part of light impinging on said silver layer, above the light-transmissive layer.

In various exemplary embodiments, forming the reflection layer, arranging the light-transmissive layer and/or arranging the partly light-transmissive silver layer can comprise a physical vapor deposition method.

In various exemplary embodiments, the method can furthermore comprise roughening a surface of the silver layer by means of laser processing.

In various exemplary embodiments, a method for testing a smart card module is provided. The method can comprise irradiating a layer stack on a smart card module in accordance with various exemplary embodiments with light of a first type in such a way that the light of the first type interacts with the layer stack, detecting first combination light that has interacted with the layer stack, determining a color of the detected first combination light, irradiating the layer stack with light of a second type in such a way that the light of the second type interacts with the layer stack, detecting second combination light that has interacted with the layer stack, and determining a color of the detected second combination light, determining a color separation between the first combination light and the second combination light, and determining a test result on the basis of a comparison of the determined color separation with a target value.

In various exemplary embodiments, the light of the first type can comprise sunlight (also referred to as daylight).

In various exemplary embodiments, the light of the second type can comprise light of an illumination device of a portable data processing device.

In various exemplary embodiments, detecting the first combination light and/or detecting the second combination light can implement detecting by means of a camera of a portable data processing device.

In various exemplary embodiments, determining a color of the detected first combination light, determining a color of the detected second combination light, determining a color separation between the first combination light and the second combination light, and/or providing the test result on the basis of the comparison of the determined color separation with the target value can be carried out by means of a portable data processing device.

In various exemplary embodiments, detecting first combination light, determining a color of the detected first combination light, detecting second combination light, determining a color of the detected second combination light, determining a color separation between the first combination light and the second combination light and determining a test result on the basis of a comparison of the determined color separation with a target value can be carried out by means of a visual inspection.

In various exemplary embodiments, the method can furthermore comprise arranging a light source for irradiating the layer stack with the light of a second type at a predetermined angle and a predetermined distance relative to a surface of the layer stack.

In various exemplary embodiments, the method can furthermore comprise detecting third combination light that has interacted with the further layer stack, during the process of irradiating the layer stack with the light of a first type, determining a color of the detected third combination light, detecting fourth combination light that has interacted with the further layer stack, during the process of irradiating the layer stack with the light of a second type, determining a color of the detected fourth combination light, determining a further color separation between the third combination light and the fourth combination light, and providing a test result on the basis of a comparison of the determined color separation with a target value and of the determined further color separation with a further target value.

In various exemplary embodiments, the method can furthermore comprise determining an additional color separation between the first combination light and the third combination light, wherein providing a test result can be furthermore based on the determined additional color separation.

Those skilled in the art will recognize additional features and advantages upon reading the following detailed description, and upon viewing the accompanying drawings.

BRIEF DESCRIPTION OF THE DRAWINGS

In the drawings, similar reference signs usually refer to the same parts in all the different views, wherein provision of all mutually corresponding parts with reference signs in all figures is dispensed with in some instances for the sake of clarity. Parts of the same or a similar type may be provided with an appended digit or an appended letter in addition to a common reference sign, for differentiation purposes. The drawings are not necessarily intended to present a reproduction that is true to scale; rather, the emphasis is on elucidating the principles of the invention. In the following description, various embodiments of the invention are described with reference to the following drawings, in which:

FIG. 1A shows a schematic cross-sectional view of a smart card module in accordance with various exemplary embodiments;

FIG. 1B shows a schematic cross-sectional view of the smart card module from FIG. 1A with an illustration of an interaction of the smart card module with incident light in accordance with various exemplary embodiments;

FIGS. 1C and 1D each show a schematic cross-sectional view of a smart card module in accordance with various exemplary embodiments;

FIG. 8 shows a flow diagram of a method for testing a smart card module in accordance with various exemplary embodiments.

DETAILED DESCRIPTION

Figure 2:
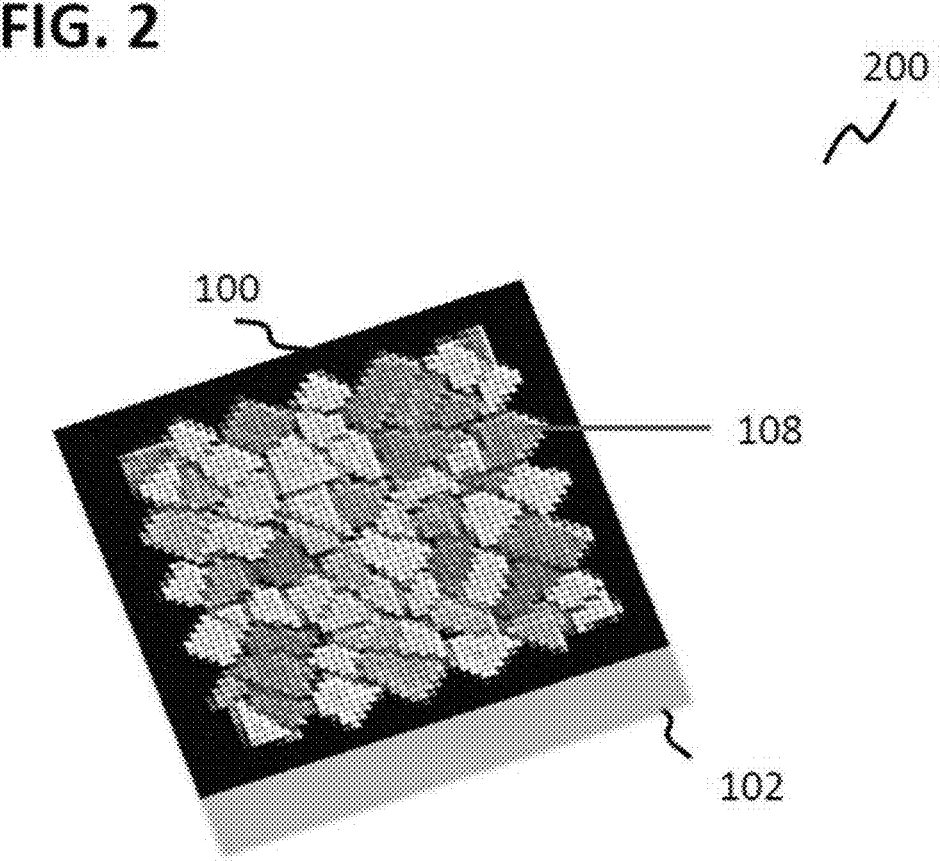
FIG. 2 shows a schematic perspective plan view of a smart card module in accordance with various exemplary embodiments.

The following detailed description refers to the accompanying drawings, which show as an example by illustration specific details and embodiments in which the invention can be implemented in practice.

The word "exemplary" is used herein in the meaning of "serving as an example, an exemplar or an illustration". All embodiments or configurations described herein as "exemplary" should not necessarily be interpreted as preferred or advantageous vis-à-vis other embodiments or configurations.

The word "above" used with reference to a deposited material formed "above" a side or surface can be used herein in the meaning that the deposited material can be formed "directly thereon", i.e. in direct contact with the indicated side or surface. The word "above" used with reference to a deposited material formed "above" a side or surface can be used herein in the meaning that the deposited material can be formed "directly on" the indicated side or surface with one or more additional layers arranged between the indicated side or surface and the deposited material.

FIG. 1A, FIG. 1B, FIG. 1C and FIG. 1D each show a schematic cross-sectional view of a smart card module 100 (100a, 100c and 100d, respectively) in accordance with various exemplary embodiments, wherein an interaction of the smart card module 100 with incident light is illustrated in FIG. 1B.

As illustrated in FIGS. 1A, 1B, 1C and 1D, the smart card module 100 in accordance with various exemplary embodiments can comprise a carrier 102 and a layer stack 105 at least partly covering the carrier. In various exemplary embodiments, the carrier 102 can be formed like an arbitrary conventional carrier 102 of a smart card module, for example with regard to material, dimensions, etc. The material of the carrier 102 can comprise for example any expedient type of material, e.g. plastic, glass, ceramic, metal (e.g. as a leadframe or lamina) or a semiconductor material, e.g. silicon.

In various exemplary embodiments, the layer stack 105 can comprise a reflection layer 104. In various exemplary embodiments, the reflection layer 104 (also referred to as mirror layer) can be designed as a metallic reflector. The reflection layer can comprise for example aluminum (Al), titanium (Ti), iron (Fe) and/or chromium (Cr), other metals and/or alloys. Furthermore, the reflection layer can comprise silicon. In a case where the carrier comprises the same material as the reflection layer, the carrier 102 and the reflection layer 104 can be formed integrally.

1 In various exemplary embodiments, the reflection layer 104 can have a thickness in a range of approximately 5 nm to approximately 500 nm, for example in a range of approximately 30 nm to approximately 50 nm, for example as a chromium layer having a thickness in a range of approximately 30 nm or of approximately 50 nm.

In various exemplary embodiments, the layer stack 105 can comprise a light-transmissive layer 106 arranged above the reflection layer 104.

In various exemplary embodiments, the light-transmissive layer 106 can be translucent or transparent. In various exemplary embodiments, the light-transmissive layer 106 can comprise a transparent oxide, for example $SiO_2$, $SiO_xN_y$, SiN, ITO or $ZrO_x$, or a transparent nitride.

In various exemplary embodiments, a thickness of the light-transmissive layer 106 can be designed such that a constructive interference for generating interference light 112_2 (illustrated in FIG. 1B as a superimposition of light reflected at the reflection layer 104 and at a surface of the light-transmissive layer 106) is made possible for at least one wavelength of light 110 impinging on the silver layer 108.

In various exemplary embodiments, the thickness of the light-transmissive layer 106 can be in a range of approximately 40 nm to approximately 400 nm.

In various exemplary embodiments, the thickness of the light-transmissive layer 106 can be chosen depending on a wavelength to be achieved or a wavelength range to be achieved of the interference light 112_2.

In various exemplary embodiments, the layer thickness of the light-transmissive layer 106 for enabling a constructive interference in a wavelength range of blue light can be in a range of approximately 70 nm to approximately 110 nm, e.g. of approximately 80 nm to approximately 100 nm. The light-transmissive layer 106 can comprise for example an $SiO_2$ layer having a thickness of 80 nm±5 nm or an indium tin oxide (ITO) having a thickness of approximately 125 nm.

In various exemplary embodiments, the layer thickness of the light-transmissive layer 106 for enabling a constructive interference in a wavelength range of yellow light can be in a range of approximately 120 nm to approximately 180 nm, e.g. of approximately 135 nm to approximately 165 nm.

In various exemplary embodiments, the layer stack 105 can comprise a partly light-transmissive silver layer 108 arranged above the light-transmissive layer 106.

The partly transmissive silver layer 108 can be configured to reflect part of light 110 impinging on said silver layer (see FIG. 1B) (illustrated as reflected light 112_1).

In various exemplary embodiments, a thickness of the partly light-transmissive silver layer 108 can be in a range of approximately 1 nm to approximately 25 nm, for example in a range of approximately 1 nm to approximately 10 nm. The partly transmissive silver layer 108 can have for example a thickness of 11 nm±3 nm or of 1-2 nm.

Figure 5:
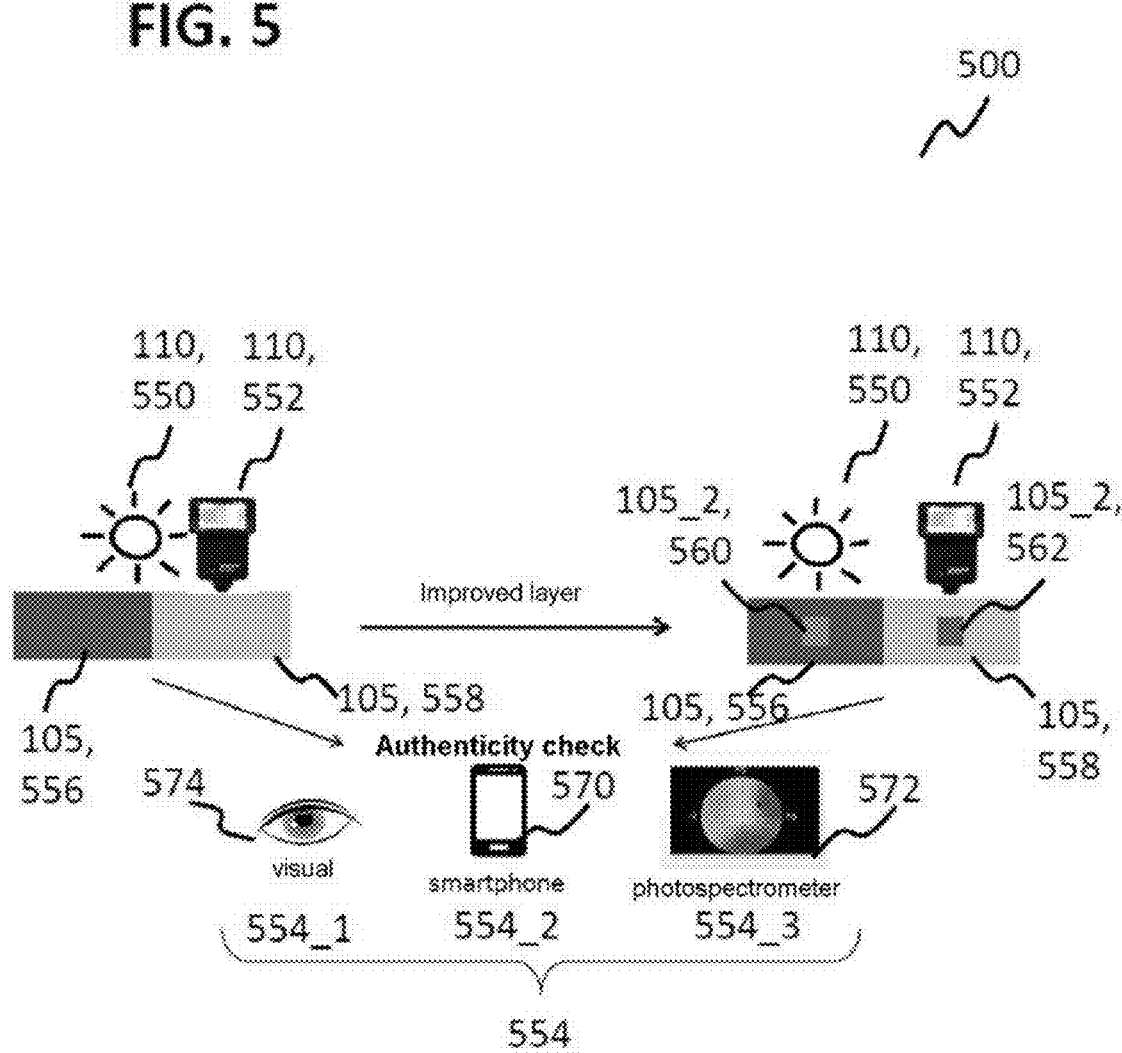
FIG. 5 and FIG. 6 each show an illustration of a method for testing a smart card module.
Figure 6:
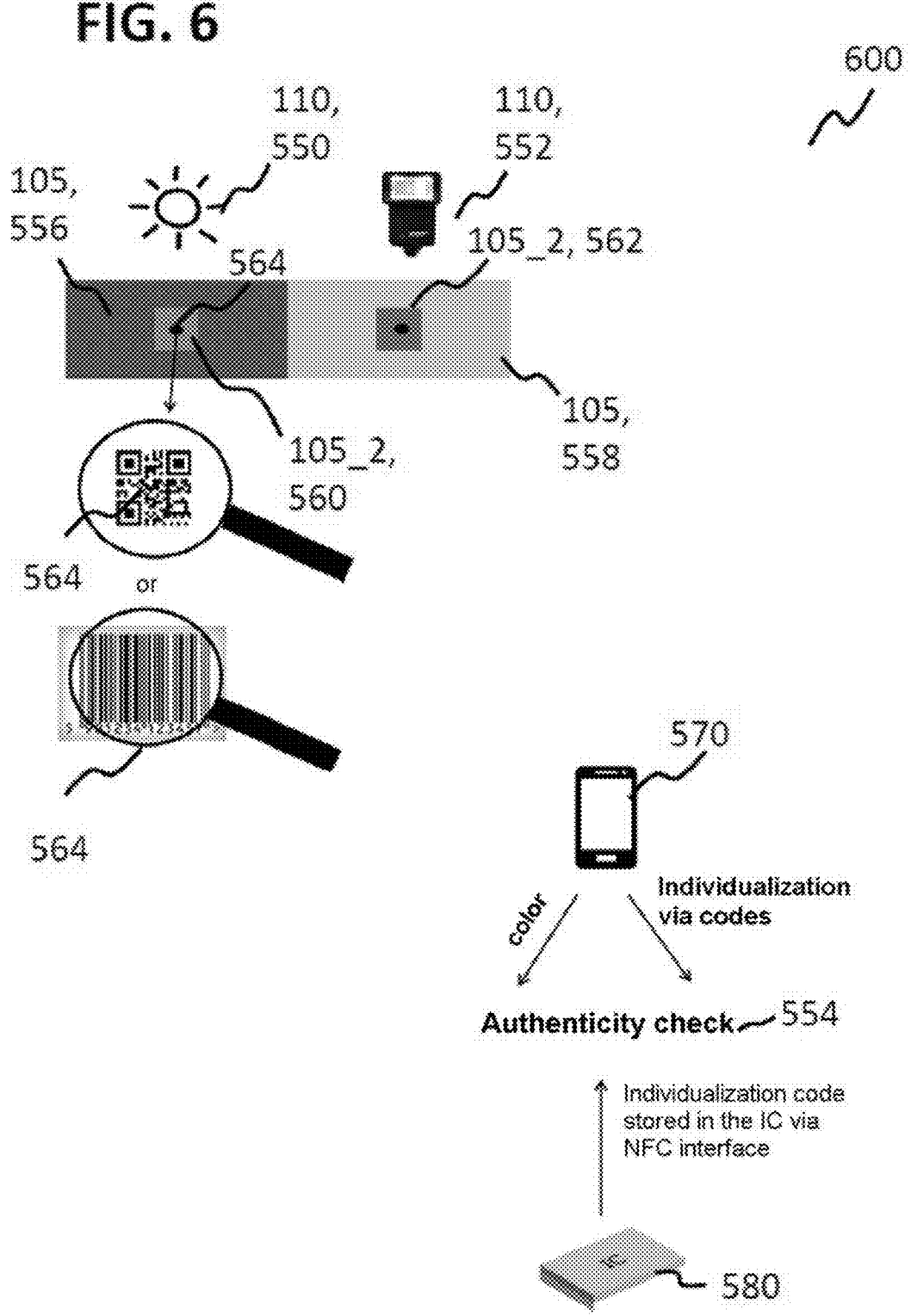

FIG. 5 and FIG. 6 each show an illustration 500 and 600, respectively, of a method for testing a smart card module 100.

In various exemplary embodiments, the layer stack 105 can be configured for forming combination light 112 from the reflected light 112_1 and the interference light 112_2 upon irradiation with light 110 and can be configured in such a way that the combination light 112 has a first combination color 556 upon irradiation with a first type of light 550 (e.g. daylight, i.e. sunlight), and that the combination light has a second combination color 558 upon irradiation with a second type of light 552 (FIG. 5 and FIG. 6 illustrate by way of example a flash light, which can be e.g. a flash light of a smartphone), wherein the spectrum of the first type of light 550 and a spectrum of the second type of light 552 differ from one another at least in a wavelength range of the interference light 112_2, such that the first combination color 556 differs from the second combination color 558. In various exemplary embodiments, on account of easy availability, it is possible to use the combination of first type of light 550 as sunlight and second type of light 552 as flash light of a smartphone 570. However, in various exemplary embodiments, it is possible to use any other combinations of light sources having a known spectrum, provided that their spectra differ from one another at least in a wavelength range of the interference light 112_2 of the layer stack 100.

In various exemplary embodiments, the smart card module 100 can furthermore comprise a further layer stack 105_2 (illustrated as a schematic plan view in FIG. 5 and FIG. 6), which can be arranged in a different region of the surface of the smart card module 100 than the layer stack 105. The further layer stack 105_2 can be configured in such a way that the combination light 112 has a third combination color 560 upon irradiation with the first type of light 550, and that the combination light 112 has a fourth combination color 562 upon irradiation with the second type of light 552, wherein a spectrum of the first type of light 550 and a spectrum of the second type of light 552 can differ from one another at least in a wavelength range of the interference light 112 of the further layer stack 105_2, such that the third combination color 560 differs from the fourth combination color 562.

In various exemplary embodiments, the first combination color 556 and the third combination color 560 can have a color separation from one another which is less than a color difference perception threshold for a human being, for example a color separation $\Delta E<1$. This can make it possible to design a color test area comprising the first layer stack 105 and the second layer stack 105_2 on the smart card module 100 in such a way that a uniformly colored area appears upon illumination of the smart card module 100 with the first type of light 550 (e.g. daylight), and the design of the color test area becomes visually recognizable only upon illumination with the second type of light 552.

In various exemplary embodiments, the first combination color 560 and the third combination color can have a color separation from one another which is greater than or equal to a color difference perception threshold for a human being, for example a color separation $\Delta E \geq 1$. This can make it possible, already upon the illumination of the smart card module 100 with the first type of light 550, to provide a colored design of the color test area, for example in order to clarify what structures will be relevant to the color change, as position marking for a recording of an image for numerically detecting the color difference or the like.

In various exemplary embodiments, more than two layer stacks 105 can be provided for the purpose of generating more than two colors.

As is illustrated in FIG. 2 on the basis of a schematic perspective view 200 of the smart card module 100, the silver layer 108 can have a rough surface structure, such that the reflected part 112_1 of light 110 impinging on it is diffusely reflected.

As shown by the illustration, the roughness of the surface can act like many small mirrors (as nanomorphology) which are not aligned exactly parallel to one another, but nevertheless anisotropically reflect incident light, this also being referred to as diffusely reflect. That can be understood to mean that a large proportion of incident light is reflected back into a small angular range—in comparison with a half-space—around a mirror direction of a smooth (ideal) mirror.

In various exemplary embodiments, the partly transmissive silver layer 108 can thus be provided as a layer which exhibits properties both of a scattering surface and of a specularly reflective surface, which is utilized when checking authenticity of the smart card module 100 using the layer stack 105, for example by taking account of angle-dependent intensities resulting therefrom.

In various exemplary embodiments, the smart card module 100, as illustrated in FIG. 1C, can furthermore comprise at least one electrically insulating cover layer 114 arranged above the silver layer 108.

In various exemplary embodiments, the electrically insulating cover layer 114 can be a transparent cover layer. In various exemplary embodiments, the cover layer 114 can comprise a nitride and/or an oxide, e.g. Si3N4, SiOx, a lacquer, and/or some other type of transparent layer, for example for protecting the layer stack against mechanical damage and/or weather influences, etc.

In various exemplary embodiments, the electrically insulating cover layer 114 can have a thickness in a range of approximately 1 nm to approximately 400 nm, e.g. an Si3N4 layer having a thickness of 30 nm±5 nm or an ITO layer having a thickness of approximately 125 nm.

In various exemplary embodiments, the smart card module 100, as illustrated in FIG. 1D, can furthermore comprise at least one electrically conductive cover layer 116 arranged above the silver layer 108 (and, if appropriate, above the electrically insulating cover layer 114), for example for producing an electrically conductive contact and/or for producing mechanical and/or physical protection. The electrically conductive cover layer can comprise for example gold (Au), titanium (Ti) or some other suitable material, for example having a thickness in a range of approximately 2 nm to approximately 25 nm, for example a gold layer having a thickness of approximately 11 nm.

Figure 3A:
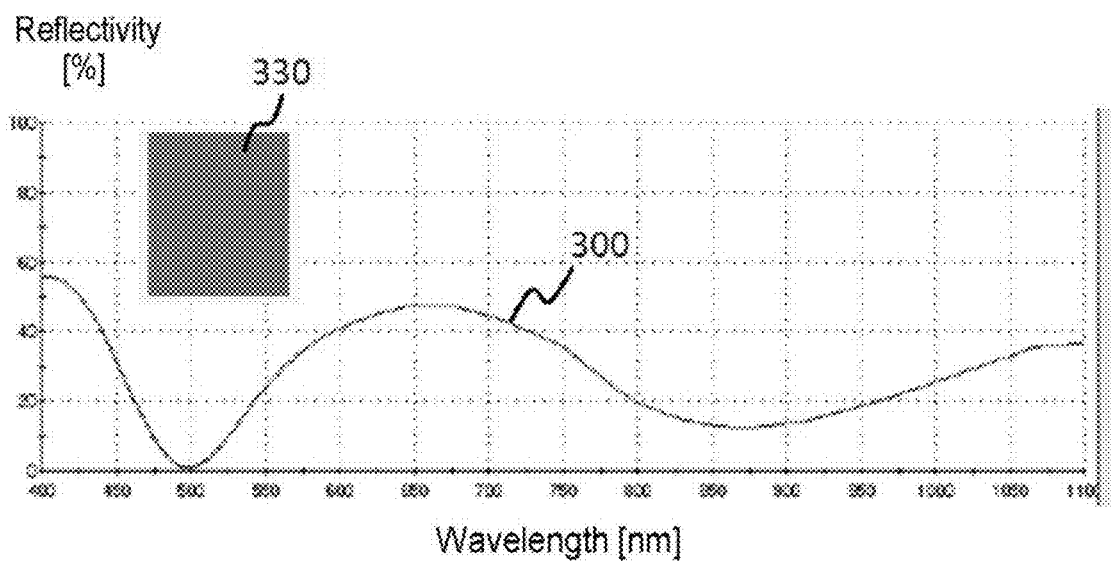
FIG. 3A and FIG. 3B each show a reflection spectrum of a layer stack in accordance with various exemplary embodiments and an illustration of a color which the respective layer stack would exhibit upon illumination with daylight.
Figure 3B:
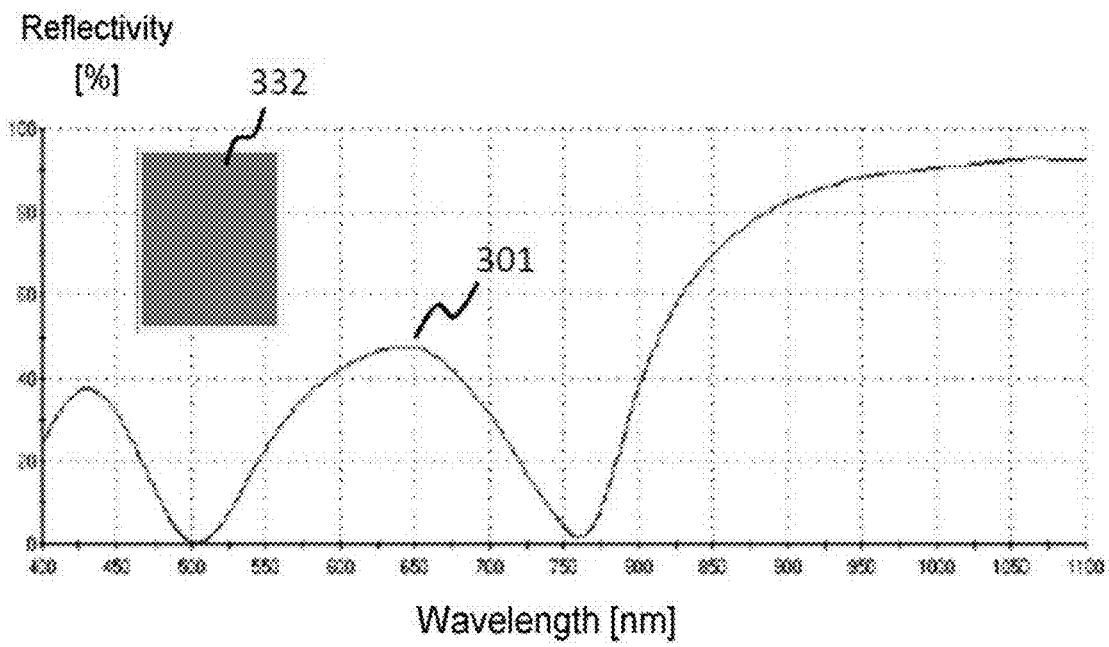

FIG. 3A and FIG. 3B each show a reflection spectrum (300 and 301, respectively) of two different layer stacks in accordance with various exemplary embodiments and a respective illustration (330 and 332, respectively) of a color which the respective layer stack would exhibit on illumination with daylight.

As is evident on the basis of the reflection spectrum 300, owing to the reflection maxima which lie in the visible range at approximately 650 nm (red) and at below 450 nm (blue to violet), the layer stack having the reflection spectrum 300 would appear red/purple to a human observer. For a spectrometer or a sensor that is sensitive in the near-infrared range, upon illumination with light 110 having a near-infrared component, an average reflectivity, which is approximately 35% in the visible range, would not be significantly changed, since an average reflectivity in the near-infrared range (beyond approximately 780 nm) is approximately 32% for the reflection spectrum 300, i.e. the layer stack from FIG. 3A reflects relatively little in the NIR range.

As is evident on the basis of the reflection spectrum 301, owing to the reflection maxima which lie in the visible range at approximately 650 nm (red) and at below 450 nm (blue to violet), the layer stack having the reflection spectrum 301 would appear red/purple to a human observer. The reflection spectra 300 and 301 can be so similar to one another that their color separation is so small that their colors are indistinguishable or almost indistinguishable to a human observer upon illumination with visible light.

For a spectrometer or a sensor which is sensitive in the near-infrared range, upon illumination of the layer stack from FIG. 3B with light 110 having a near-infrared component, an average reflectivity, which is approximately 35% in the visible range, would be greatly increased, since an average reflectivity in the near-infrared range (beyond approximately 780 nm) is almost 80% for the reflection spectrum 301, i.e. the layer stack from FIG. 3A reflects very well in the NIR range.

In various exemplary embodiments, by way of example, the layer stack to which the reflection spectrum from FIG. 3B is assigned can be mounted on a smart card module 100 in accordance with various exemplary embodiments in order to enable a "color" change (between quotation marks because strictly speaking a color perception is not assigned to the near-infrared range as non-visible range) that does not arise in the visual spectral range, but rather only in the near-infrared range, upon irradiation with a first type of light 550, which comprises no or little near-infrared light, and a second type of light 552, which comprises a great deal of near-infrared light. For testing the smart card module it is possible to use a sensor that is sensitive in the near-infrared range, for example a smartphone camera, a near-infrared photometer, near-infrared spectrometer and/or a near-infrared spectrophotometer.

For the layer stack in accordance with FIG. 3A, as light of the first type 550 and light of the second type it is possible to use, for example, light which differs in a spectral range around 500 nm (reflection minimum) or around 650 nm (reflection maximum).

As is illustrated in FIG. 5 and FIG. 6, in various exemplary embodiments, an authenticity check 554 can be carried out as a visual authenticity check 554_1 (i.e. by means of a human observer 574), as an authenticity check 554_2 by means of a portable data processing device 570, and/or as an authenticity check 554_3 by means of a special measuring device 572, for example a photospectrometer or some other suitable device, for example as described elsewhere herein.

As is illustrated in FIG. 6, in various exemplary embodiments, a code 564, e.g. a QR code or a barcode, may have been or can be applied on the smart card module 100 in such a way that it has been or is mounted on the layer stack 100 and/or on the geometric pattern. This can make it possible to generate a forgery-proof QR code/barcode that can be used for individualization/personalization.

For the individualization/personalization and/or for an additional security level, in various exemplary embodiments, encrypted information of the QR code/barcode can additionally be stored in a chip (e.g. in the integrated circuit (IC) 580) and be read out as necessary, e.g. by means of NFC, e.g. by means of the smartphone or some other suitable reader. In accordance with various exemplary embodiments, the layer stack 100 having optionally extendable security can provide multilevel security.

Figure 4:
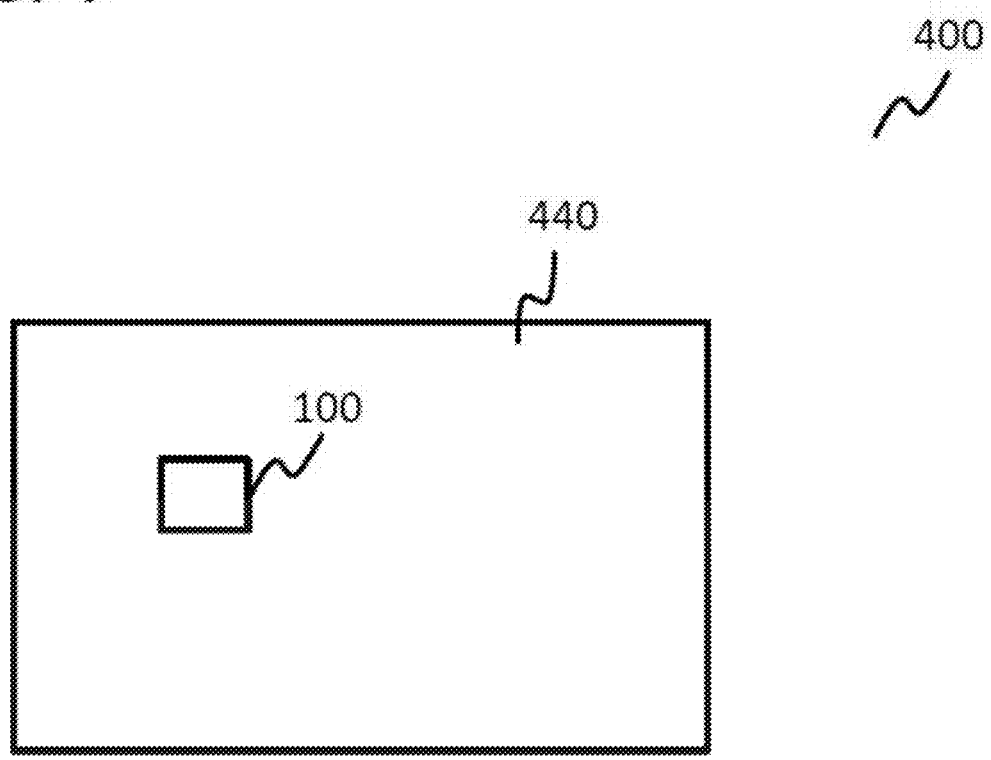
FIG. 4 shows a schematic illustration of a smart card in accordance with various exemplary embodiments.

FIG. 4 shows a schematic illustration of a smart card 400 in accordance with various exemplary embodiments.

In various exemplary embodiments, the smart card can comprise a smart card body 440 and a smart card module 100 in accordance with various exemplary embodiments embedded into the smart card body 440. The smart card body 440 can be a conventional smart card body 440. The smart card module 100 can be arranged in the smart card body 440 in such a way that the layer stack 105 is at least partly not covered or covered only by light-transmissive material.

Figure 7:
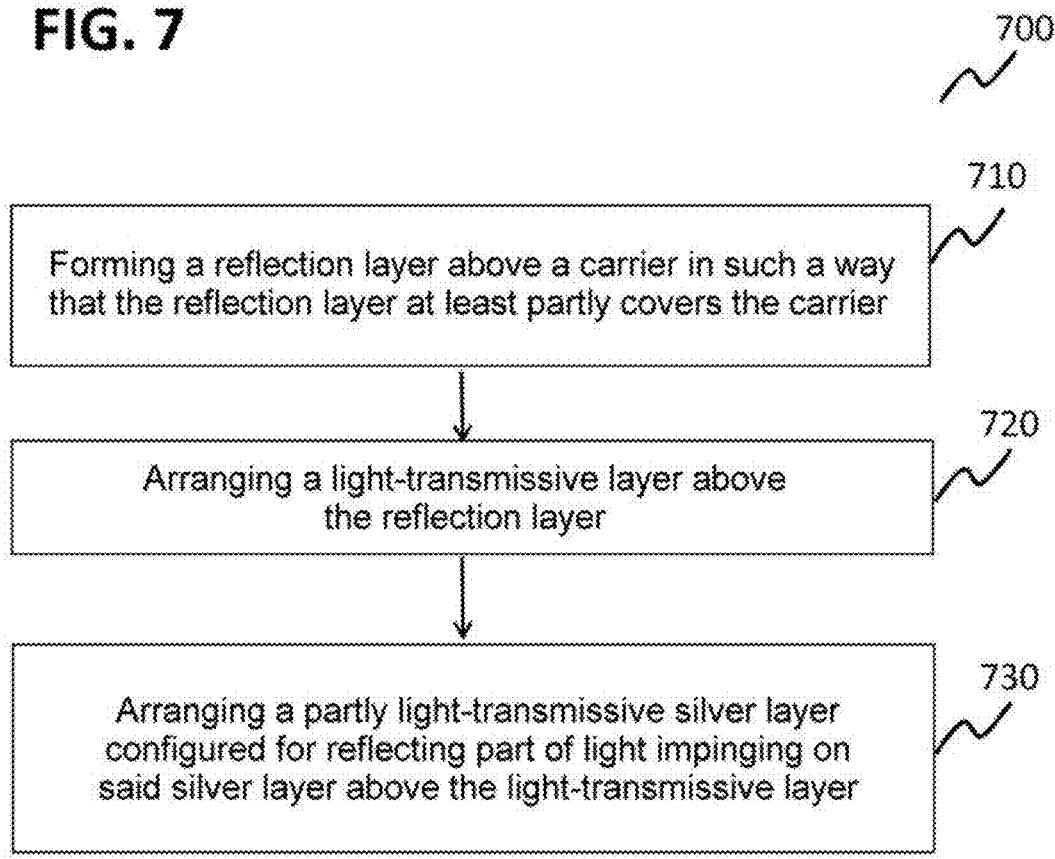
FIG. 7 shows a flow diagram of a method for producing a smart card module in accordance with various exemplary embodiments.

FIG. 7 shows a flow diagram 700 of a method for producing a smart card module in accordance with various exemplary embodiments.

The method can comprise forming a reflection layer above a carrier, in such a way that the reflection layer at least partly covers the carrier (in 710), arranging a light-transmissive layer above the reflection layer (in 720), and arranging a partly light-transmissive silver layer, which can be configured for reflecting part of light impinging on said silver layer, above the light-transmissive layer (in 730).

In various exemplary embodiments, forming the reflection layer (in 710), arranging the light-transmissive layer (in 720) and/or arranging the partly light-transmissive silver layer (in 730) can comprise a physical vapor deposition method.

In various exemplary embodiments, the method can furthermore comprise roughening a surface of the silver layer by means of laser processing. A resulting structuring of the surface of the silver layer can comprise, as described above, a plurality of small mirror surfaces.

FIG. 8 shows a flow diagram 800 of a method for testing a smart card module 100 in accordance with various exemplary embodiments.

The method can comprise irradiating a layer stack on a smart card module in accordance with various exemplary embodiments with light of a first type, in such a way that the light of the first type interacts with the layer stack (in 810), detecting first combination light that has interacted with the layer stack (in 820), determining a color of the detected first combination light (in 830), irradiating the layer stack with light of a second type in such a way that the light of the second type interacts with the layer stack (in 840), detecting second combination light that has interacted with the layer stack (in 850), determining a color of the detected second combination light (in 860), determining a color separation between the first combination light and the second combination light (in 870), and determining a test result on the basis of a comparison of the determined color separation with a target value (in 880).

In various exemplary embodiments, the light of the first type 550 can comprise sunlight (also referred to as daylight).

In various exemplary embodiments, the light of the second type 552 can comprise light of an illumination device of a portable data processing device.

In various exemplary embodiments, detecting the first combination light and/or detecting the second combination light can implement detecting by means of a camera of a portable data processing device (e.g. a smartphone, a tablet or the like).

In various exemplary embodiments, determining a color of the detected first combination light, determining a color of the detected second combination light, determining a color separation between the first combination light and the second combination light, and/or providing the test result on the basis of the comparison of the determined color separation with the target value can be carried out by means of a portable data processing device (e.g. a smartphone, a tablet or the like), e.g. by means of software, e.g. an app.

In various exemplary embodiments, detecting first combination light, determining a color of the detected first combination light, detecting second combination light, determining a color of the detected second combination light, determining a color separation between the first combination light and the second combination light and determining a test result on the basis of a comparison of the determined color separation with a target value can be carried out by means of a visual inspection 554_1.

This can be used for example if the color separation between the first combination light and the second combination light is large by comparison with a color separation that is indiscernible to the naked eye, for example for $\Delta E \gg 1$.

Examples thereof are illustrated in FIG. 5 and FIG. 6, with a blue color 556 of the first combination light and a yellow color 558 of the second combination light.

In various exemplary embodiments, the method can furthermore comprise arranging a light source for irradiating the layer stack with the light of a second type at a predetermined angle and a predetermined distance relative to a surface of the layer stack.

In various exemplary embodiments, the method can furthermore comprise arranging a camera for detecting the combination light (e.g. the first or the second combination light) at a predetermined angle and a predetermined distance relative to a surface of the layer stack. In various exemplary embodiments, a position mark arranged on the layer stack can be used for this purpose, for example, as described above. For complying with the predetermined angle, for example of an optical axis of an entrance opening of a camera perpendicular or substantially with respect to a surface of the layer stack, the smart card module can be positioned, and the camera (e.g. a smartphone camera), by means of an auxiliary device, e.g. a spirit level displayed on its display, can be equipped for arranging the camera at a predetermined angle relative to the surface of the layer stack, e.g. with a predetermined orientation of the smartphone.

With use of other devices for detecting the combination light, corresponding apparatuses can be used in a substantially known manner in order to achieve predefined relative positionings.

In various exemplary embodiments, the method can furthermore comprise detecting third combination light that has interacted with the further layer stack, during the process of irradiating the layer stack with the light of a first type, determining a color of the detected third combination light, detecting fourth combination light that has interacted with the further layer stack, during the process of irradiating the layer stack with the light of a second type, determining a color of the detected fourth combination light, determining a further color separation between the third combination light and the fourth combination light, and providing a test result on the basis of a comparison of the determined color separation with a target value and of the determined further color separation with a further target value.

In the example illustrated in FIG. 5 and FIG. 6, respectively, a color separation between the color 560 of the third combination light (green) and a color of the fourth combination light (red) can likewise be large enough to be identified by means of a visual detection 554_1.

In various exemplary embodiments, alternatively or additionally, as described elsewhere herein, detecting the combination light, determining the colors and the color separation and comparing with a color separation target value, for example attaining a predefined tolerance range around a target value, or attaining a minimum color separation, can be performed by means of suitable other devices.

In various exemplary embodiments, the other devices can be suitable for example in cases in which a quantitative analysis or an automatic detection is desired or required, and/or in a case where the color difference becomes apparent in the non-visible range.

In various exemplary embodiments, the method can furthermore comprise determining an additional color separation between the first combination light and the third combination light, wherein providing a test result can furthermore be based on the determined additional color separation. By means of utilizing two or more layer stacks for providing two or more color changes, a reliability of the test method can furthermore be increased.

Some of the exemplary embodiments have been described in association with devices, and some of the exemplary embodiments have been described in association with methods. Further advantageous configurations of the method are evident from the description of the device, and vice versa.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A smart card module, comprising:
    a carrier;
    a layer stack at least partly covering the carrier and comprising:
        a reflection layer;
        a light-transmissive layer arranged above the reflection layer; and
        a partly light-transmissive silver layer arranged above the light-transmissive layer and configured for reflecting part of light impinging on the partly light-transmissive silver layer;
    a QR code or barcode on the layer stack; and
    a chip in which encrypted information of the QR code or barcode is stored.

2. The smart card module of claim 1, wherein the light-transmissive layer has a thickness such that a constructive interference for generating interference light is made possible for at least one wavelength of light impinging on the partly light-transmissive silver layer.

3. The smart card module of claim 2, wherein the thickness of the light-transmissive layer is in a range of approximately 40 nm to approximately 400 nm.

4. The smart card module of claim 1, wherein the light-transmissive layer has a thickness for enabling a constructive interference in a wavelength range of blue light and which is in a range of approximately 70 nm to approximately 110 nm.

5. The smart card module of claim 1, wherein the light-transmissive layer has a thickness for enabling a constructive interference in a wavelength range of yellow light and which is in a range of approximately 120 nm to approximately 180 nm.

6. The smart card module of claim 1, wherein the partly light-transmissive silver layer has a thickness in a range of approximately 2 nm to approximately 25 nm.

7. The smart card module of claim 1, wherein the partly light-transmissive silver layer has a rough surface structure such that the reflected part of light impinging on the partly light-transmissive silver layer is diffusely reflected.

8. The smart card module of claim 1, wherein the layer stack is configured for forming combination light from the reflected light and the interference light upon irradiation with light, and is configured such that the combination light has a first combination color upon irradiation with a first type of light, and that the combination light has a second combination color upon irradiation with a second type of light, wherein a spectrum of the first type of light and a spectrum of the second type of light differ from one another at least in a wavelength range of the interference light such that the first combination color differs from the second combination color.

9. The smart card module of claim 8, further comprising:
    a further layer stack configured such that the combination light has a third combination color upon irradiation with the first type of light, and that the combination light has a fourth combination color upon irradiation with the second type of light,
    wherein a spectrum of the first type of light and a spectrum of the second type of light differ from one another at least in a wavelength range of the interference light of the further layer stack, such that the third combination color differs from the fourth combination color.

10. The smart card module of claim 9, wherein the first combination color and the third combination color have a color separation with respect to one another which is less than a color separation $\Delta E < 1$.

11. The smart card module of claim 1, further comprising:
    at least one electrically insulating or electrically conductive cover layer arranged above the partly light-transmissive silver layer.

12. A smart card, comprising:
    a smart card body; and
    the smart card module of claim 1 embedded into the smart card body.

13. A method for producing a smart card module, the method comprising:
    forming a reflection layer above a carrier, which has a chip, such that the reflection layer at least partly covers the carrier;
    arranging a light-transmissive layer above the reflection layer;
    arranging a partly light-transmissive silver layer configured for reflecting part of light impinging on the partly light-transmissive silver layer above the light-transmissive layer;
    applying a QR code or barcode on the smart card module; and
    storing encrypted information of the QR code or barcode in the chip.

14. The method of claim 13, wherein forming the reflection layer, arranging the light-transmissive layer and/or arranging the partly light-transmissive silver layer comprises a physical vapor deposition method.

15. The method of claim 14, further comprising:
    roughening a surface of the partly light-transmissive silver layer by means of laser processing.

16. A method for testing a smart card module that includes a carrier, a layer stack at least partly covering the carrier and including a reflection layer, a light-transmissive layer arranged above the reflection layer and a partly light-transmissive silver layer arranged above the light-transmissive layer and configured for reflecting part of light impinging on the partly light-transmissive silver layer, a QR code or barcode on the layer stack, and a chip in which encrypted information of the QR code or barcode is stored, the method comprising:
    irradiating the layer stack with light of a first type such that the light of the first type interacts with the layer stack;
    detecting a first combination light that has interacted with the layer stack;
    determining a color of the detected first combination light;
    irradiating the layer stack with light of a second type such that the light of the second type interacts with the layer stack;
    detecting a second combination light that has interacted with the layer stack;
    determining a color of the detected second combination light;
    determining a color separation between the first combination light and the second combination light;

determining a test result based on a comparison of the determined color separation with a target value; and
comparing encrypted information provided by means of the QR code or barcode with the encrypted information stored in the chip.

17. The method of claim 16, wherein the light of the first type comprises sunlight.

18. The method of claim 16, wherein the light of the second type comprises light of an illumination device of a portable data processing device.

19. The method of claim 16, wherein the first combination light and/or the second combination light is detected by means of a camera of a portable data processing device.

20. The method of claim 16, wherein the layer stack is configured for forming combination light from the reflected light and the interference light upon irradiation with light, and is configured such that the combination light has a first combination color upon irradiation with a first type of light, and that the combination light has a second combination color upon irradiation with a second type of light, wherein a spectrum of the first type of light and a spectrum of the second type of light differ from one another at least in a wavelength range of the interference light such that the first combination color differs from the second combination color, the method further comprising:
 during the process of irradiating the layer stack with the light of a first type, detecting a third combination light that has interacted with the further layer stack;
 determining a color of the detected third combination light;
 during the process of irradiating the layer stack with the light of a second type, detecting a fourth combination light that has interacted with the further layer stack;
 determining a color of the detected fourth combination light;
 determining a further color separation between the third combination light and the fourth combination light; and
 providing a test result based on a comparison of the determined color separation with a target value and of the determined further color separation with a further target value.

21. The method of claim 20, further comprising:
 determining an additional color separation between the first combination light and the third combination light, wherein providing the test result is further based on the determined additional color separation.

* * * * *